United States Patent [19]
Flocée

[11] 3,950,651
[45] Apr. 13, 1976

[54] METHOD AND AN ARRANGEMENT FOR DEFINING A RADIATION TREATMENT FIELD

[76] Inventor: Rune E. Flocée, Vasterled 25, Bromma, Sweden

[22] Filed: Nov. 6, 1974

[21] Appl. No.: 521,276

[52] U.S. Cl. .................................................. 250/505
[51] Int. Cl.² ........................................... G21F 5/04
[58] Field of Search ........................... 250/505, 514

[56] References Cited
UNITED STATES PATENTS

| | | | |
|---|---|---|---|
| 3,114,043 | 12/1963 | Thomas | 250/505 |
| 3,227,880 | 1/1966 | Wideroe | 250/505 |
| 3,755,672 | 8/1973 | Edholm | 250/510 |

Primary Examiner—Craig E. Church
Attorney, Agent, or Firm—Wolfe, Hubbard, Leydig, Voit & Osann

[57] ABSTRACT

A method of defining the radiation beam for medical therapy in which the beam is shaped by an aperture in an easily formable, radiation absorbing member. The member is formed by compressing a mixture of granulated heavy metal, such as tungsten, with powdered pressure sensitive adhesive into a shape-retaining box. The member is cut to define the aperture desired, and preferably the cutting is done so that the aperture walls parallel the beam that will pass therethrough.

3 Claims, 4 Drawing Figures

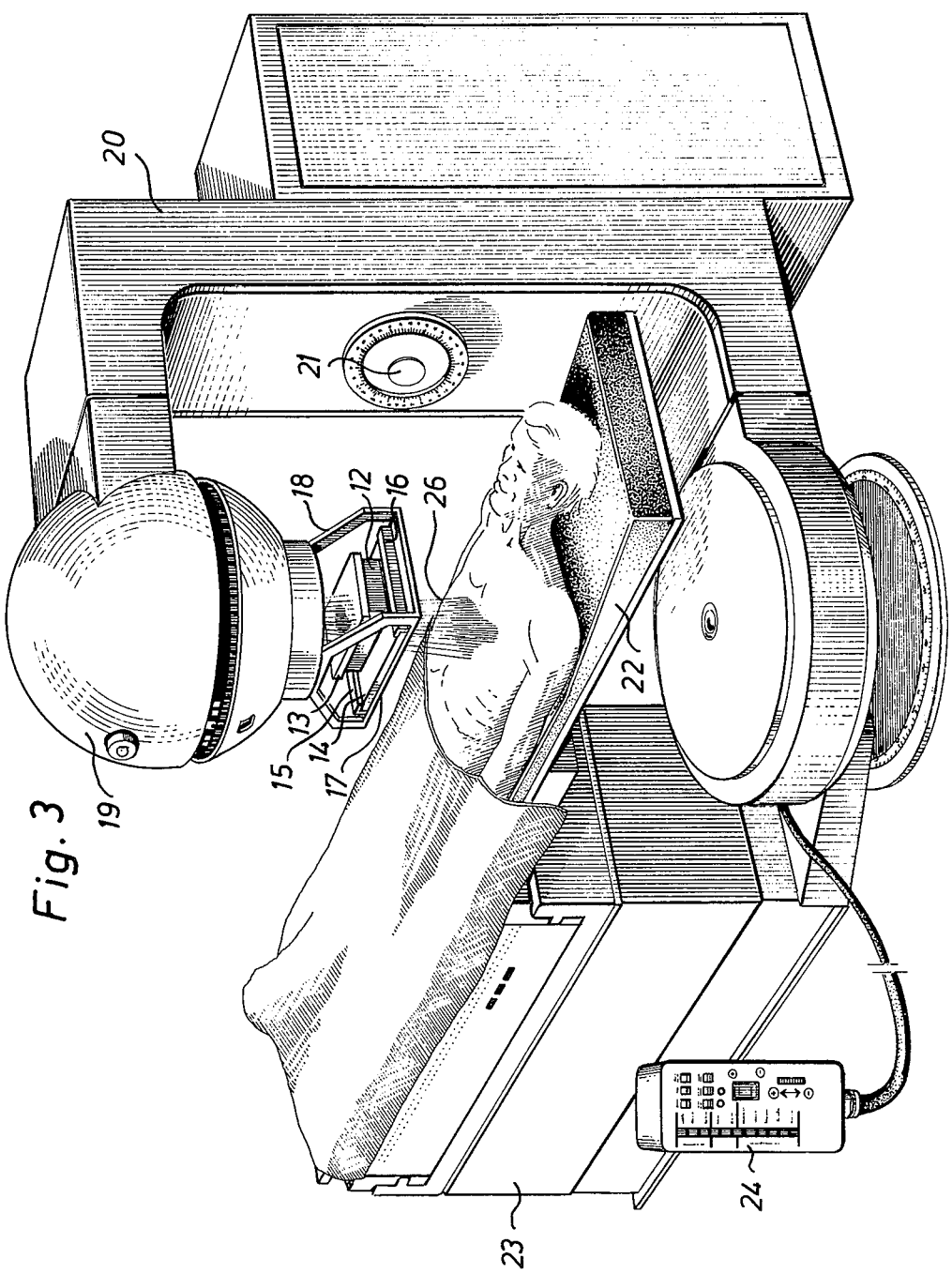

METHOD AND AN ARRANGEMENT FOR DEFINING A RADIATION TREATMENT FIELD

The present invention relates generally to equipment for defining the field, or target area, to be radiated in the medical treatment of patients and, more particularly, patients suffering from cancer, malign tumours, or similar diseases.

As is well-known, when a patient is to be treated by radiation for the purposes above mentioned, the first step to be carried out by the medical experts is to define the desired target area. This is usually made by X-raying. The target areas vary from different patients not only in terms of location on the patient but also as far as their sizes and shapes are concerned. By way of example, in the treatment of lung cancer, it is not unusual to have a target area covering say one lung. Accordingly, such target areas often have very irregular contours. This circumstance coupled with the fact that it is necessary on the one hand to make sure that the radiation reaches all of the target area and, on the other, does not hurt adjacent tissues not affected by the disease, involves that the target area must be determined and defined with great accuracy. A third factual circumstance to be noticed in this context is that patients suffering from cancer have to be treated on repeated occasions, typically once a week for several months. The radiation is emitted by a radiation source mounted inside a therapeutic unit and it emerges therefrom through an aperture in a shutter carried by that unit. That aperture is generally of circular or rectangular cross-section and it is consequently necessary downstream thereof to modify the effective cross-section of the radiated beam so that it matches the contour of the target area. This is in prior art arrangements made by the use of blocks consisting of a radiation-absorbing material, generally lead. From what has been said above it is apparent that each time a certain patient is to be radiation-treated a number of such blocks have to be arranged so that the target area is properly defined. It is common practice to mark that area on the body of the patient and during the arrangement of the absorption blocks to have the apparatus emit ordinary light through said aperture so that the proper configuration of the blocks can be checked.

A major disadvantage of the method above accounted for is that the block arrangement work has to be repeated on each treatment occasion. A second disadvantage is that the patient has to be present during the corresponding time period. This does not only mean that the patient has to be in the treatment room for a considerably longer period of time than that during which he is treated but also correspondingly reduces the availability of the most expensive equipment for the treatment of further patients.

The main object of the present invention is to eliminate the disadvantages and shortcomings above referred to. A method for defining the target area to be radiated in the treatment of such a patient is, according to the present invention, characterised by the steps of mixing a heavy metal fine grain powder with a pressure-sensitive, non-curing adhesive so that a plastically deformable composition is formed, compressing a disc-shaped member consisting of said composition for the purpose of increasing its density and geometrical stability, providing said member with a through aperture the contour of which is congruent with that of said target area, and mounting said member between the shutter and the target area in such a position that the contour of said second aperture is located inside the cross-section of the beam.

The invention does also concern a composition for use in the carrying out of the above defined method and a therapy unit constructed so as to operate according to the method.

One embodiment of the invention will now be described in greater detail, reference being made to the accompanying drawing, on which:

FIG. 3 is a perspective view showing a therapy unit designed in accordance with the teachings of this invention.

Figure 1:
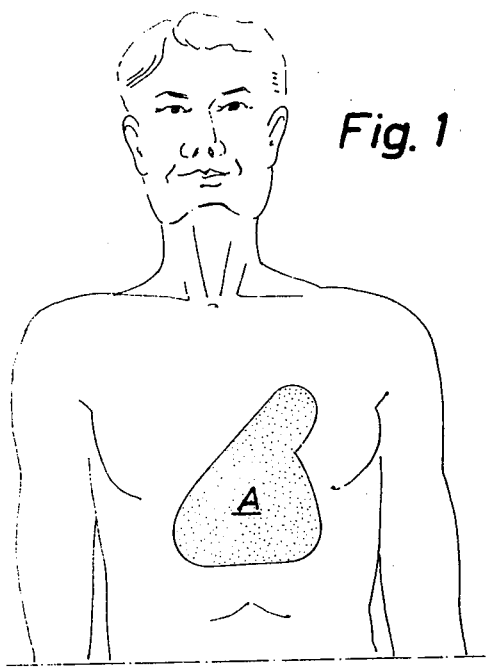
FIG. 1 shows a portion of a human body with a radiation target area marked thereon.
Figure 2:
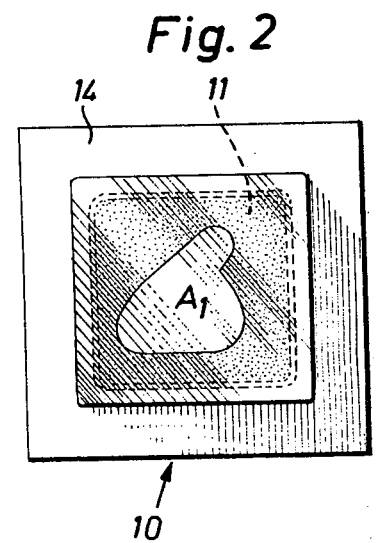
FIG. 2 illustrates a device for matching the cross-section of a radiated beam to the desired target area.

The invention is based on the realization that it is possible to modify the effective cross-section of the radiated beam by means of a device which could be looked upon as a secondary shutter the aperture of which is in a disc- or frame-like member consisting of a composition having special properties. The composition consists of a heavy metal, such as tungsten or lead, in powder form the individual grains of the powder being held together by an adhesive which does not cure with time. The adhesive is of the type known as "pressure-sensitive adhesives" which means that its binding action is dependent of the external pressure to which the cemented product, i.e. in this case the metal powder member, is subjected. The amount of pressure to be applied cannot be specified generally, as it is a function of the particular metal chosen, of its grain size and of the relative amount of adhesive used, etc. However, the skilled worker does not encounter any difficulties in rapidly finding the pressure to be used for certain selected values of the other parameters so that he can produce a composition exhibiting the following two valuable properties. On the one hand, it has in contrast to a solid metal block such a high softness that cuts therein can readily be made by means of an ordinary knife, a cutting wire or the like. On the other hand, although it has that consistency it is stable enough to maintain the shape which has been given to a product made therefrom. The net result is that such a composition can be used for the provision of a beam contour modifying device, or shutter, the cross-section of whose aperture conforms exactly with the contour of the target area, or treatment field. This is in sharp contrast to prior art devices where the field contour can only be simulated approximately in the sense that curved lines have to be composed by a plurality of short straight lines, each defined by one radiation absorption block. In addition thereto, it is generally necessary to arrange such blocks in two or more layers and the result is that the border of the beam is not sharply defined. Instead, penumbras arise.

It should also be understood that there is, according to this invention, no need for using either the therapeutic unit or a special, also very expensive, simulator for the construction of the beam cross-section modifying device nor does the patient have to be present when this working step is performed. Also, once such a device has been made and used in the first corresponding treatment of the patient it can be saved and is immediately available for the succeeding treatments thus doing away with the need of having to repeat the time-consuming beam-modifying operation each time a treatment shall be repeated. Moreover, when the patient has received his final treatment so that the device is no more needed as far as he is concerned, the composition contained in his shutter is immediately available for the construction of similar devices for other patients.

The manufacture of a composition rendering itself for the use above referred to will now be described. A tungsten powder (available on the market) having a grain size which preferably is in the interval 200–325 mesh according to U.S. standard is mixed with a small amount of a pressure-sensitive adhesive, typically 1–10% by weight. The two ingredients are mixed in a suitable agitating machine until the operator visually establishes that they have formed a homogenous mass. According to a preferred embodiment of the invention the next step is to put an adequate amount of the mass in a box made of a transparent material, such as MACROLON (Registered Trademark). That box is then snugly surrounded by a reinforcing metal frame and placed in a press the piston of which is lowered towards the top surface of the mass. This compaction procedure does only require a few seconds and the resulting product can be described as a disc- or block-shaped member constituting a shutter blank.

The next step is to cut out the shutter aperture. This operation can be performed in several different manners. By way of example, the cutting tool can be remote-controlled by a sensor which is manually or automatically caused to track the contour line of the target area as marked on an X-ray photo.

While the invention is not limited to the use of any special radiation source in the therapy unit but can be successfully worked with all types of radiation generators, such as betatrons and linear accelerators, it is of special value when the radiation source is constituted by a radioactive sample, usually cobalt 60. Such a sample performs as a point-shaped radiation source and does consequently, in principle, emit a conical beam. By letting the cutting tool pivot around a point at the same distance from the shutter under manufacture as the distance between the focus of the beam and the shutter as installed in the therapy unit, one achieves that the walls of the aperture will be parallel to the radially outermost rays passing through the aperture. As is directly understood, this represents a perfect solution of the penumbra problem.

As has already been indicated, upon completion of the cutting operation the final step is to mount the shutter in its desired position. In many applications it is most practical to modify the therapy unit so that its source head supports also the shutter. However, in special cases a member serving as a shutter can also be inserted into the patient's body, orally, rectally, or vaginally. When it forms a portion of the unit proper the latter can conveniently be provided with position-fixing means so that the only adjustment work necessary in preparation of the treatment is correctly to position the patient on the treatment couch, to slide his individual shutter into its position and in the conventional manner, using ordinary light, to check that the beam area projected on the body of the patient coincides with the desired field.

In FIG. 1 there has diagrammatically been shown a portion of a patient's body on which a desired treatment area A has been marked. Reference numeral 10 designates a box-like shutter the aperture of which has a cross-sectional area $A_1$ which is congruent with area A. The aperture has been provided by a cutting operation as above described. It is accordingly surrounded by a, in this case square, disc-like member 11 consisting of a composition comprising the two ingredients also above specified. As is most clearly seen from FIG. 4, the composition is housed in a box 12 made of a transparent material, such as MACROLON. It has a lid 13 and a larger bottom 14 which rests on cross bars 17 and is held in position by guide rails 15, 16. The latter can consequently receive boxes 10 which can be larger or smaller than that shown in FIG. 4 as long as they are mounted on identical bottom plates 14.

The arrangement just described is supported by brackets 18 depending from the lower portion of a source head 19. This is carried by a so-called C-arm 20, which can pivot around a horizontal axis 21 as is well-known in the art. The patient is in FIG. 3 shown resting on a treatment couch 22 supported by a base 23 to which there is connected a control box 24 for the operation of the unit.

Figure 4:
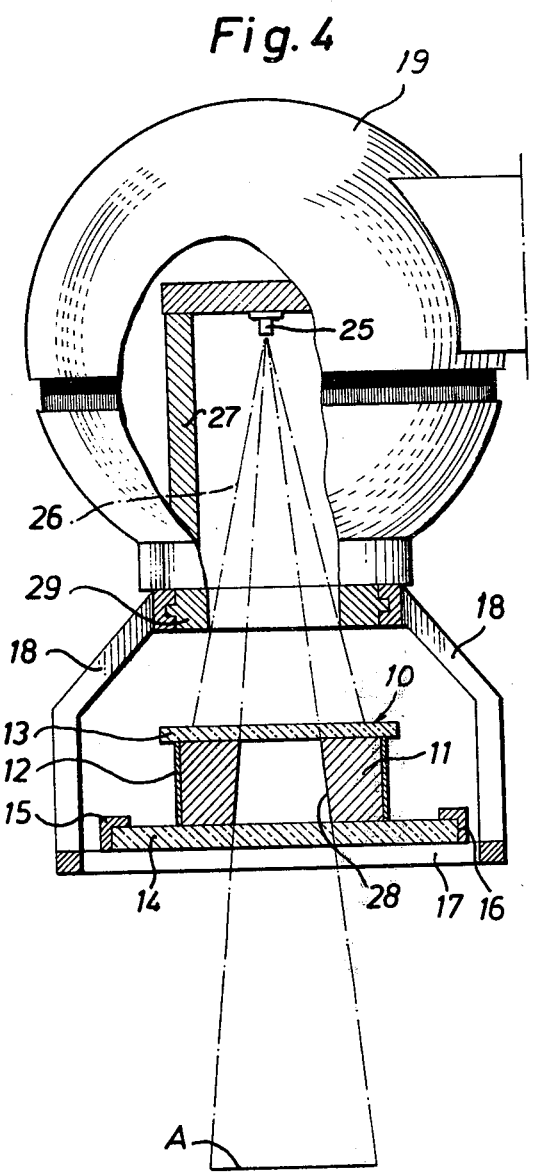
FIG. 4 is a part-sectional elevation view of the source head of the unit of FIG. 3.

Reference numeral 25 refers to the radiation source, in this case a sample of a radioactive material, e.g. cobalt 60. It is surrounded by a radiation protection cylinder 27 and emits a conical beam 26 the radially outward rays of which first hit a conventional primary shutter 29. The aperture thereof limits the cross-section of the beam so that at the level of the top of box 12 all beams either hit the radiation-protective material 11 or pass through the aperture of shutter 10. FIG. 4 illustrates how, thanks to the above-described way of providing that aperture, the walls 28 thereof are parallel to the border rays thus doing away with the penumbra problem.

It is evident that in the practical working of the invention it can be modified in several respects as compared to the embodiment thereof here selected to illustrate the basic inventive concept. This is especially true as far as the relative dimensions of the shutter arrangement are concerned. When the treatment field location is to be checked in the conventional optical way it is convenient to house material 11 in a box having at least its bottom and a lid made of a transparent material. However, in other applications material 11 can be confined in any other suitable way. It should also be understood that other metals than tungsten may be used, especially lead.

What is claimed is:

1. The method of shaping a radiation beam for the treatment of patients so that the beam cross-section conforms to the target area to be treated, comprising, in combination, the steps of mixing a volume of fine grain, heavy metal powder with a quantity of pressure sensitive, non-curing adhesive so as to form a mass of plastically deformable, radiation absorbable material, compressing said material into a block-like member of sufficient area to block said beam and sufficient thickness, considering the compressed density of the material, to absorb the radiation energy of said beam, said compression having the effect of increasing the density of said member and making that member geometrically stable, removing material from said member to form an aperture therethrough having a peripheral contour corresponding to the contour of said target area, and mounting said member in said beam so that said aperture permits a beam of the desired cross sectional shape and size to fall on said target area.

2. The method of claim 1 including the step of facilitating handling of said plate by supporting the member on a radiation transparent support plate, and covering said member with a radiation transparent cover plate, so as to protect the formed periphery of said aperture.

3. The method of claim 1 in which said powder is tungsten in a grain size on the order of 200–325 mesh, and said adhesive is present in an amount in the order of 1 to 10% by weight.

* * * * *